United States Patent [19]

Villa et al.

[11] Patent Number: 5,663,432
[45] Date of Patent: Sep. 2, 1997

[54] PROCESS FOR THE PREPARATION OF 5-AMINO-2,4,6-TRIIODOISOPHTHALIC ACID DICHLORIDE BY CHLORINATION WITH THIONYL CHLORIDE IN THE PRESENCE OF A CATALYST

[75] Inventors: Marco Villa, Milan; Claudio Pozzoli, Monza; Laura Russo, Milan; Graziano Castaldi, Briona, all of Italy

[73] Assignee: Zambon Group S.p.A., Vicenza, Italy

[21] Appl. No.: 649,490

[22] Filed: May 17, 1996

[30] Foreign Application Priority Data

May 18, 1995 [IT] Italy .................................. MI95A1004

[51] Int. Cl.$^6$ .................................................. C07C 63/00
[52] U.S. Cl. ............................................................ 562/855
[58] Field of Search ................................................ 562/855

[56] References Cited

U.S. PATENT DOCUMENTS

| | | |
|---|---|---|
| 3,655,752 | 4/1972 | Ackerman et al. . |
| 4,250,113 | 2/1981 | Nordal et al. . |

FOREIGN PATENT DOCUMENTS

| | | |
|---|---|---|
| 0 026 281 | 4/1981 | European Pat. Off. . |
| 0 083 964 | 7/1983 | European Pat. Off. . |
| 0 118 347 | 9/1984 | European Pat. Off. . |
| 825418 | 7/1977 | France . |
| 1472050 | 4/1977 | United Kingdom . |
| WO91/09007 | 6/1991 | WIPO . |
| WO93/10825 | 6/1993 | WIPO . |
| WO96/16927 | 6/1996 | WIPO . |

OTHER PUBLICATIONS

Kenneth A. Burdett, "An Improved Acid Chloride Preparation Via Phase Transfer Catalysis", Syntheses, pp. 441–442, Jun. 1991.

*Primary Examiner*—Paul J. Killos
*Attorney, Agent, or Firm*—Oblon, Spivak, McClelland, Maier & Neustadt, P.C.

[57] ABSTRACT

A process for the preparation of 5-amino-2,4,6-triiodoisophthalic acid dichloride by chlorination of 5-amino-2,4,6-triiodoisophthalic acid with thionyl chloride in the presence of a suitable solvent characterized in that the reaction is carried out in the presence of catalytic amounts of a tetraalkylammonium salt of formula $$R_1R_2R_3R_4NX \qquad (I)$$

wherein X is halogen, mesylate or tosylate; $R_1$, $R_2$, $R_3$ and $R_4$, the same or different, are $C_1$–$C_{20}$ alkyl groups so that the total number of carbon atoms of the groups $R_1$, $R_2$, $R_3$ and $R_4$ is higher than 16.

The 5-amino-2,4,6-triiodoisophthalic acid dichloride obtained according to the process of the present invention is useful as intermediate in the synthesis of iodinated contrast media.

10 Claims, No Drawings

PROCESS FOR THE PREPARATION OF 5-AMINO-2,4,6-TRIIODOISOPHTHALIC ACID DICHLORIDE BY CHLORINATION WITH THIONYL CHLORIDE IN THE PRESENCE OF A CATALYST

The present invention relates to a process for the preparation of an intermediate useful in the synthesis of organic compounds and, more particularly, it relates to a process for the preparation of 5-amino-2,4,6-triiodoisophthalic acid dichloride.

5-Amino-2,4,6-triiodoisophthalic acid dichloride is a known compound useful for the preparation of iodinated contrast media among which we can cite Iopamidol (British patent no. 1,472,050—Savac AG), Iohexol (U.S. Pat. No. 4,250,113—Nyegaard & Co.) and Ioversol (European patent application no. 0 083 964—Mallinckrodt Inc.).

Several examples of synthesis of 5-amino-2,4,6-triiodoisophthalic acid dichloride are reported in the literature and all of them foresee the chlorination of 5-amino-2,4,6-triiodoisophthalic acid with thionyl chloride.

In particular, we can cite the syntheses described in the already mentioned British patent no. 1,472,050, in the Belgian patent no. 852,418 (Mallinckrodt Inc.) and in the U.S. Pat. No. 3,655,752 (Sterling Drug Inc.) which use a large excess of thionyl chloride and which require a long and cumbersome work-up, difficulty suitable from the industrial view-point, even though sometimes they allow to obtain the desired dichloride with high yields.

Also the synthesis described in the European patent application no. 0 118 347 (Guerbet S.A.) foresees the use of thionyl chloride in excess but in the presence of catalytic amounts of N,N-dimethylformamide. The yields are high but, also in this case, the work-up needs the removal of the excess thionyl chloride by evaporation.

The use of solvents such as ethyl acetate, as described in the International patent applications no. WO 91/09007 (Mallinckrodt Inc.) and no. WO 93/10825 (Mallinckrodt Inc.) or in the already cited European patent application no. 0 083 964, does not allow to obtain the desired dichloride with satisfactory yields.

The European patent application no. 0 026 281 (Bracco Industria Chimica S.p.A.) describes the preparation of 5-methylamino-2,4,6-triiodoisophthalic acid dichloride by reaction with thionyl chloride in the presence of small amounts of quinoline, without reporting the yields yet. The International patent application No. PCT/EP95/04635, filed on Nov. 24, 1995 in the name of the same Applicant, describes a process for the preparation of 5-amino-2,4,6-triiodoisophthalic acid dichloride by chlorination with thionyl chloride characterized in that the reaction is carried out in the presence of a salt of a tertiary amine or of a quaternary ammonium in a molar ratio from 1:1 to 1:2 with respect to 5-amino-2,4,6-triiodoisophthalic acid.

The use of catalytic amounts of benzyltriethylammonium chloride or betaine in the preparation of acid chlorides has been described in Synthesis, Jun 1991, pages 441–442.

We have now found that, by using a tetraalkylammonium salt of formula $$R_1R_2R_3R_4NX \qquad (I)$$

wherein X is halogen, mesylate or tosylate; $R_1$, $R_2$, $R_3$ and $R_4$, the same or different, are $C_1$–$C_{20}$ alkyl groups so that the total number of carbon atoms of the groups $R_1$, $R_2$, $R_3$ and $R_4$ is higher than 16;

the chlorination reaction of 5-amino-2,4,6-triiodoisophthalic acid with thionyl chloride occurs with high yields and with the same degree of purity even if in the presence of catalytic amounts of said tetraalkylammonium salt.

Therefore, object of the present invention is a process for the preparation of 5-amino-2,4,6-triiodoisophthalic acid dichloride by chlorination of 5-amino-2,4,6-triiodoisophthalic acid with thionyl chloride in the presence of a suitable solvent characterized in that the reaction is carried out in the presence of catalytic amounts of a tetraalkylammonium salt of formula $$R_1R_2R_3R_4NX \qquad (I)$$

wherein X is halogen, mesylate or tosylate; $R_1$, $R_2$, $R_3$ and $R_4$, the same or different, are $C_1$–$C_{20}$ alkyl groups so that the total number of carbon atoms of the groups $R_1$, $R_2$, $R_3$ and $R_4$ is higher than 16.

The 5-amino-2,4,6-triiodoisophthalic acid dichloride obtained according to the process object of the present invention is useful as intermediate in the synthesis of iodinated contrast media. The amount of thionyl chloride used in the process object of the present invention is generally between 2 and 6 moles with respect to 5-amino-2,4,6-triiodoisophthalic acid.

Preferably, from 3 to 4 moles of thionyl chloride for mole of 5-amino-2,4,6-triiodoisophthalic acid are used.

For catalytic amount of tetraalkylammonium salt of formula I a molar amount from 0.3 to 10% with respect to 5-amino-2,4,6-triiodoisophthalic acid is intended.

Preferably, a molar amount of compound of formula I from 1 to 5% is used.

The compounds of formula I which can be used in the process object of the present invention are preferably compounds wherein X is chlorine, bromine, mesylate or tosylate; $R_1$, $R_2$, $R_3$, $R_4$, the same or different, are $C_1$–$C_{20}$ alkyl groups so that the total number of carbon atoms is from 25 to 38.

Specific examples of preferred compounds of formula I are trioctylmethylammonium, methyl-trialkyl($C_8$–$C_{10}$) ammonium, dioctadecyldimethylammonium and tridodecylmethylammonium chlorides, bromides, mesylates or tosylates, which can be optionally prepared in situ from the corresponding tertiary amine and from the suitable alkyl chloride, bromide, mesylate or tosylate.

For practical and economical reasons trioctylmethylammonium chloride, commercialized as Aliquat 336® (registered trademark of Henkel Corporation), and methyltrialkyl-($C_8$–$C_{10}$)ammonium chloride, commercialized as Adogen 446® (registered trademark of Ashland Chemical Co.) are preferably used.

Suitable solvents are ethyl acetate, toluene, methylene chloride, 1,2-dichloroethane, isopropyl acetate and mixture thereof.

Preferably, toluene is used.

The reaction temperature is not a critical parameter and it can range from 20° C. to the reflux temperature.

Preferably, the chlorination process object of the present invention is carried out at warm at a temperature from 60° C. to 90° C.

A preferred practical embodiment of the present invention is the following.

A catalytic amount of a tetraalkylammonium salt of formula I is added to a suspension of 5-amino-2,4,6-triiodoisophthalic acid in a suitable solvent.

After heating to the reaction temperature, thionyl chloride is added dropwise to the suspension.

The resultant solution is kept at the reaction temperature for some hours.

At the end of the reaction, the mixture is cooled at room temperature and water is added observing the precipitation of a crystalline product.

By simple filtration and washing, 5-amino-2,4,6-triiodoisophthalic acid dichloride is obtained in pure form.

The characterizing feature of the present invention is the presence of a tetraalkylammonium salt as catalyst.

As far as we know, there are no examples of preparation of 5-amino-2,4,6-triiodoisophthalic acid dichloride by reaction with thionyl chloride in the presence of a tetraalkylammonium salt as a catalyst in the literature.

The use of this kind of catalyst allows to achieve a number of advantages with respect to the prior art, such as extremely high yields and decrease in the amount of thionyl chloride to be used, but mainly a significant decrease of reaction by-products which make difficult the isolation of 5-amino-2,4,6-triiodoisophthalic acid dichloride with a degree of purity suitable for the use as intermediate in the synthesis of iodinated contrast media.

The improvement of the reaction yields and the decrease of the impurities with respect to the reactions for the preparation of 5-amino-2,4,6-triiodoisophthalic acid dichloride described in the literature is proved by the comparison between the results obtained in example 10, wherein the procedure described in the British patent no. 1,472,050 was used, and in example 11, wherein the procedure described in the International patent application no. WO 91/09007 was used, and the results obtained in examples 1–9 and 12–13, according to the process object of the present invention.

It is worth underlining that the substantial absence of by-products in the reaction for the preparation of 5-amino-2,4,6-triiodoisophthalic acid dichloride according to the process object of the present invention does not result exclusively in an improvement of the overall yield of the process with respect to the known methods, but allows also the isolation of the desired product by simple treatment with water of the reaction mixture.

Furthermore, by using catalytic amounts of tetraalkylammonium salt it is possible to carry out the reaction with an amount of thionyl chloride only slightly in excess with respect to the stoichiometric amount without lowering the reaction yield yet.

It is clear to the man skilled in the art the advantage deriving from the possibility of carrying out the process for the synthesis of an intermediate with high yields, high purity, through extremely simple work-up, without the need of removing thionyl chloride by evaporation or repeating purification procedures for the isolation of the desired product in pure form.

As already underlined, contrary to what described for the known processes for the preparation of 5-amino-2,4,6-triiodoisophthalic acid dichloride, the isolation of the pure product is carried out by simple treatment of the reaction mixture with water.

On the base of our knowledge, a mechanism able to explain the unexpected advantages deriving from the use of a tetraalkylammonium salt as catalyst according to the process of the present invention cannot be hypothesized.

In this connection, however, it is worth noting that the use of quinoline or of a tetraalkylammonium salt having a total number of carbon atoms lower than or equal to 16, such as for example benzyltriethylammonium chloride, as catalysts in the reaction between thionyl chloride and 5-amino-2,4,6-triiodoisophthalic acid does not allow to obtain the desired product with a suitable degree of purity (see example 14).

In order to better illustrate the present invention, the following examples are now given.

EXAMPLE 1

In a 500 ml reactor equipped with magnetic stirrer, thermometer and reflux condenser with florentine flask, 5-amino-2,4,6-triiodoisophthalic acid (KF=3.44%; 150 g; 0.259 moles) and toluene (173 g) were charged under inert atmosphere.

After azeotropic distillation of water, the mixture was cooled at 85° C. and Aliquat 336® (5.25 g; 0.013 moles) was added.

By keeping under stirring, thionyl chloride 97% (111.6 g; 0.91 moles) was added dropwise in 3 hours.

At the end of the addition, the reaction mixture was kept at 85° C. for 4 hours.

After cooling at room temperature water (16.4 g) was added dropwise.

After addition of a seed of 5-amino-2,4,6-triiodoisophthalic acid dichloride, the mixture was kept under stirring for about 16 hours, the solid filtered and triturated with toluene (30 g) and then dried in oven under vacuum (40° C.—30 mmHg) for about 18 hours obtaining 5-amino-2,4,6-triiodoisophthalic acid dichloride (141 g; 88% yield) with 96.5% titre.

EXAMPLES 2–11

By working as described in example 1 the experiments 2–9 reported in the table were carried out.

Experiments 10 and 11 were carried out by using the procedures described in the British patent no. 1,472,050 and in the International patent application no. WO 91/09007, respectively.

TABLE

| Example | Solvent | Concentration[a] | Catalyst[b] (% mole) | Temperature (°C.) | Time (hours) | Yield (titre) | Impurity (HPLC area %) |
|---|---|---|---|---|---|---|---|
| 2 | toluene | 600 | 5% | 85 | 4 | 90.6% (97.7%) | 2.1 |
| 3 | ethyl acetate | 300 | 10% | 75 | 24 | 78.5% (98.3%) | 1.1 |
| 4 | toluene | 300 | 10% | 85 | 4 | 80% | 1.9 |
| 5 | toluene | 1200 | 5% | 85 | 4 | 92% (95%) | 2.4 |
| 6 | toluene | 1200 | 1% | 85 | 4 | 90% (96.5%) | 3.0 |
| 7 | toluene | 600 | 2.5% | 85 | 4 | 87% (99%) | 2.2 |
| 8 | toluene | 1000 | 2.5% | 85 | 4 | 90.6% (98.5%) | 2.5 |
| 9 | toluene:methylene chloride = 1:1 | 1000 | 5% | 60 | 4 | 87% | 3.5 |
| 10[c] | — | — | — | 72 | 6 | 71.6% | >18 |
| 11[c] | ethyl acetate | 600 | — | 75 | 20 | 60% | >5 |

[a]concentrations expressed as grams of 5-amino-2,4,6-triiodoisophtalic acid/liters of solvent
[b]Aliquat 336 ® - percentage expressed with respect to molar amount of 5-amino-2,4,6-triiodoisophthalic acid
[c]Comparative examples

EXAMPLE 12

In a 500 ml reactor equipped with magnetic stirrer, thermometer and reflux condenser with florentine flask, 5-amino-2,4,6-triiodoisophthalic acid (KF=2.96%; 100 g; 0.173 moles) and toluene (100 g) were charged under inert atmosphere.

After azeotropic distillation of water, the mixture was cooled at 70° C. and Aliquat 336® (2.5 g; 0.006 moles) was added.

By keeping the reaction mixture under stirring at 70° C., thionyl chloride (74.5 g; 0.626 moles) was added dropwise in 16 hours.

At the end of the addition, the reaction mixture was kept at 70° C. for 4 hours.

After cooling at room temperature water (300 g) was slowly added.

After addition of a seed of 5-amino-2,4,6-triiodoisophthalic acid dichloride, the mixture was kept under stirring for about 16 hours, the solid filtered and triturated with dichloromethane and then dried in oven under vacuum for about 18 hours obtaining 5-amino-2,4,6-triiodoisophthalic acid dichloride (97.9 g; 90% yield) with 98% titre.

EXAMPLE 13

In a 100 ml reactor equipped with magnetic stirrer, thermometer and reflux condenser with florentine flask, 5-amino-2,4,6-triiodoisophthalic acid (KF=2.96%; 30 g; 52.08 mmoles) and toluene (55 g) were charged under inert atmosphere.

After azeotropic distillation of water, the mixture was cooled at 85° C. and Adogen 446® (2.5 g; 5.1 mmoles) was added.

By keeping under stirring, thionyl chloride 97% (22.1 g; 180.2 mmoles) was added dropwise in 3 hours.

At the end of the addition, the reaction mixture was kept at 85° C. for 4 hours.

After cooling at room temperature water (4 g) was slowly added.

After addition of a seed of 5-amino-2,4,6-triiodoisophthalic acid dichloride, the mixture was kept under stirring for about 16 hours, the solid filtered and triturated with toluene and then dried in oven under vacuum for about 18 hours obtaining 5-amino-2,4,6-triiodoisophthalic acid dichloride (28.5 g; 89% yield) with 97% titre.

COMPARATIVE EXAMPLE 14

In a 100 ml reactor equipped with magnetic stirrer, thermometer and reflux condenser with florentine flask, 5-amino-2,4,6-triiodoisophthalic acid (KF=1%; 13.84 g; 24.5 mmoles), 1,2-dichloroethane (45 ml) and benzyltriethylammonium chloride (0.009 g; 0.038 mmoles) were charged under inert atmosphere.

Thionyl chloride (10.62 g; 89.24 mmoles) was added to the reaction mixture under reflux.

At the end of the addition, the reaction mixture was kept under reflux for 18 hours.

After cooling at room temperature water (2 g) was slowly added.

After addition of a seed of 5-amino-2,4,6-triiodoisophthalic acid dichloride, the mixture was kept under stirring for about 16 hours, the solid filtered and triturated with dichloromethane and then dried in oven under vacuum for about 18 hours obtaining 5-amino-2,4,6-triiodoisophthalic acid dichloride (10.8 g; 61% yield) with 82.5% titre.

What we claim is:

1. A process for the preparation of 5-amino-2,4,6-triiodoisophthalic acid dichloride comprising chlorinating 5-amino-2,4,6-triiodoisophthalic acid with thionyl chloride in the presence of a suitable solvent and in the presence of a catalytic amount of tetraalkylammonium salt of the formula $$R_1R_2R_3R_4NX \qquad (I)$$

wherein X is halogen, mesylate or tosylate; $R_1$, $R_2$, $R_3$ and $R_4$, the same or different, are $C_1$–$C_{20}$ alkyl groups so that the total number of carbon atoms of the groups $R_1$, $R_2$, $R_3$ and $R_4$ is higher than 16.

2. The process according to claim 1, wherein the amount of thionyl chloride is from 3 to 4 moles with respect to 5-amino-2,4,6-triiodoisophthalic acid.

3. The process according to claim 1, wherein the tetraalkylammonium salt of formula I is in a molar amount from 0.3 to 10% with respect to 5-amino-2,4,6-triiodoisophthalic acid.

4. The process according to claim 3, wherein the molar amount of tetraalkylammonium salt is between 1 and 5% with respect to 5-amino-2,4,6-triiodoisophthalic.

5. The process according to claim 1, wherein in said tetraalkylammonium salt of formula I, X is chlorine, bromine, mesylate or tosylate; $R_1$, $R_2$, $R_3$ and $R_4$, the same or different, are $C_1$–$C_{20}$ alkyl groups so that the total number of carbon atoms is between 25 and 38.

6. The process according to claim 5, wherein the tetraalkylammonium salt of formula I is a trioctylmethylammonium, methyltrialkyl($C_8$–$C_{10}$) ammonium, dioctadecyldimethylammonium or tridodecylmethylammonium chloride, bromide, mesylate or tosylate.

7. The process according to claim 6, wherein the tetraalkylammonium salt of formula I is trioctylmethylammonium chloride or methyltrialkyl($C_8$–$C_{10}$)ammonium chloride.

8. The process according to claim 1, wherein the solvent is ethyl acetate, toluene, methylene chloride, 1,2-dichloroethane or isoproply acetate or a mixture thereof.

9. The process according to claim 8, wherein the solvent is toluene.

10. A process for the preparation of iopamidol, iohexol or ioversol comprising the preparation of 6-amino-2,4,6-triiodoisophthalic acid dichloride according to claim 1.

* * * * *